US011098273B2

(12) United States Patent
Dorignac et al.

(10) Patent No.: US 11,098,273 B2
(45) Date of Patent: Aug. 24, 2021

(54) YEAST EXTRACT FOR CLARIFYING MUSTS AND BEVERAGES

(71) Applicant: LESAFFRE ET COMPAGNIE, Paris (FR)

(72) Inventors: Etienne Dorignac, Mazeres (FR); Rudy Menin, Choisy le Roi (FR); Yves Gosselin, Allouagne (FR)

(73) Assignee: LESAFFRE ET COMPAGNIE, Paris (FR)

( * ) Notice: Subject to any disclaimer, the term of this patent is extended or adjusted under 35 U.S.C. 154(b) by 45 days.

(21) Appl. No.: 15/558,012

(22) PCT Filed: Mar. 24, 2016

(86) PCT No.: PCT/FR2016/050660
§ 371 (c)(1),
(2) Date: Sep. 13, 2017

(87) PCT Pub. No.: WO2016/151257
PCT Pub. Date: Sep. 29, 2016

(65) Prior Publication Data
US 2018/0079995 A1 Mar. 22, 2018

(30) Foreign Application Priority Data
Mar. 24, 2015 (FR) ..................................... 15 52464

(51) Int. Cl.
*C12H 1/052* (2006.01)
*A23L 2/84* (2006.01)
(Continued)

(52) U.S. Cl.
CPC ........... *C12H 1/0416* (2013.01); *A23F 3/166* (2013.01); *A23L 2/84* (2013.01); *C12N 1/063* (2013.01);
(Continued)

(58) Field of Classification Search
None
See application file for complete search history.

(56) References Cited

U.S. PATENT DOCUMENTS 5,112,627 A  *  5/1992  Perletti .................... C12G 1/02
                                                   426/236
6,139,891 A     10/2000  Dubourdieu et al.
(Continued)

FOREIGN PATENT DOCUMENTS

EP        0 299 078       1/1989
EP        1 240 306       9/2002
(Continued)

OTHER PUBLICATIONS

Eurasyp Apr. 14, 2014 2 pages http://www.yeastextract.info/news-and-downloads/news/135/natural-yeast-the-nutritious-basis-for-yeast-extract (Year: 2014).*

(Continued)

*Primary Examiner* — Felicia C Turner
(74) *Attorney, Agent, or Firm* — Duane Morris LLP; Thomas J. Kowalski; Deborah L. Lu (57) ABSTRACT

The present invention relates to the use of a yeast extract including at least 10 wt % of nucleic acids, preferably at least 15 wt %, and more preferably 30 to 95 wt %, relative to the total weight of said extract, said nucleic acids being formed from fragments of ribonucleic acid (RNA), for clarifying musts and liquids, in particular wines and teas.

13 Claims, 4 Drawing Sheets

(51) Int. Cl.
*A23F 3/16* (2006.01)
*C12N 1/06* (2006.01)
*C12G 1/022* (2006.01)
*A23L 2/70* (2006.01)
*A23L 33/14* (2016.01)

(52) U.S. Cl.
CPC .............. *A23L 2/70* (2013.01); *A23L 33/14* (2016.08); *A23V 2002/00* (2013.01); *C12G 1/0203* (2013.01)

(56) References Cited

U.S. PATENT DOCUMENTS

| | | |
|---|---|---|
| 9,084,435 B2 | 7/2015 | Iwakiri et al. |
| 2003/0162735 A1 | 8/2003 | Tkachuk |
| 2010/0178300 A1 | 7/2010 | Yiannikouris et al. |
| 2010/0303960 A1 | 12/2010 | Yu et al. |
| 2011/0020528 A1 | 1/2011 | Iwakiri et al. |
| 2015/0225690 A1 | 8/2015 | Iwakiri et al. |
| 2016/0331015 A1 | 11/2016 | Iwakiri et al. |
| 2017/0196235 A1 | 7/2017 | Nakao et al. |

FOREIGN PATENT DOCUMENTS

| | | |
|---|---|---|
| EP | 2 255 679 | 12/2010 |
| EP | 2 256 184 | 12/2010 |
| EP | 2 258 831 | 12/2010 |
| WO | 96/13571 | 5/1996 |
| WO | 01/046380 | 6/2001 |
| WO | 03/063613 | 8/2003 |
| WO | 03/063614 | 8/2003 |
| WO | 2005/013723 | 2/2005 |
| WO | 2016/010064 | 4/2017 |

OTHER PUBLICATIONS

Mitsuyanagi et al.(JP 2004229540) Derwent Abstract Aug. 19, 2004 (Year: 2004).*

Fernandes et al. Mar. 18, 2005 Frontiers in Chemistry "Unveiling the potential of novel yeasts protein extracts in white wines clarification and stabilization" pp. 1-11 (Year: 2015).*

International Search Report dated Jun. 22, 2016, which issued during prosecution of International Application No. PCT/FR2016/050660.

* cited by examiner

YEAST EXTRACT FOR CLARIFYING MUSTS AND BEVERAGES

RELATED PATENT APPLICATIONS

The present application is filed pursuant to 35 U.S.C. § 371 as a U.S. National Phase Application of International Patent Application No. PCT/FR2016/050660, which was filed on Mar. 24, 2016, claiming the benefit of priority to French Patent Application No. FR 15 52464 filed on Mar. 24, 2015. The content of each of the aforementioned Patent Applications is incorporated herein by reference in their entirety.

The subject of the present invention is the use of a yeast extract for clarifying musts and liquids, in particular beverages such as wine, tea, beer or fruit juices.

"Clarifying" is a technique which consists in introducing into a product to be treated (liquids, musts) a substance capable of flocculating and sedimenting by precipitating in its sedimentation the particles suspended in said product, this being for the purpose of improving the clarity, filterability, stability and also some organoleptic qualities of said product.

Thus, by virtue of the clarifying, the visible and/or invisible particles suspended in the product and also the colloid load, said colloids being responsible for the cloudiness and the lack of filterability of said product, are greatly reduced, or even totally eliminated.

With regard to a beverage such as wine, the lack of stability of the latter is often reflected by the appearance of deposits and/or of cloudiness due to protein degradation or to microbiological growth. Decreasing the unstable-particle load by virtue of the clarifying makes it possible to delay or limit the appearance of the deposits and/or cloudiness.

Clarifying can improve certain gustative aspects of wines, such as bitterness or astringency. However, when clarifying is poorly controlled, it can also weaken the structure and aromatic strength of certain wines.

Clarifying can also contribute to erasing certain faults or deviations generally due to poor sanitary conditions.

The clarifying of wines has been known and carried out for a very long time. It was during the XIXth century that it became systematic to carry it out, in particular on large volumes of wines. Nowadays, clarifying is carried out even by small-scale producers.

The clarifying products, hereinafter denoted "clarifiers", commonly used over the past few years in the wine sector are isinglass (which is a crude protein extracted from the swim bladders of fish), casein, egg white, animal or plant gelatins, bentonites (which are natural clays), polyvinylpyrrolidone ("PVPP", which is a synthetic product that has a high affinity for polyphenols). The PVPP clarifier is often combined with casein and makes it possible to erase the astringency of young red wines and the bitterness and yellow color of white wines.

The first four clarifiers mentioned have the drawback of being of animal origin, and can therefore pose allergenic problems. PVPP has, for its part, a chemical connotation and has a toxicity when handled.

In order to improve the quality of clarifiers for wines, research studies have related to natural products, for instance yeasts. A study from 2006 ("Revue des œnologues" ["Enologists' Review"], No. 120; pages 47-50, 2006) has thus showed that a yeast protein extract (hereinafter denoted "YPE") has a clarifying action that is equivalent to, or even better than, that of the clarifiers conventionally used.

However, there is still today a need to develop other clarifiers from natural products, which are even more efficient than the existing clarifiers, in particular in the wine sector.

Thus, one of the objectives of the invention is to provide wine producers and distributors with a natural product intended to be used in operations for clarifying musts and wines.

With regard to a beverage such as tea, it can prove necessary and advantageous to bring about the precipitation of the visible or invisible particles present in the tea, and in particular the tannins.

Indeed, a tea rich in tannins is easily recognizable by the astringency of its liquor, which sometimes becomes bitterness when the tea is too greatly infused. The tannins are slowly but increasingly released and thus an infusion that is too lengthy considerably increases their concentration and gives the tea its bitterness when the tea is too greatly infused.

Moreover, the tannins present in tea, even though they are advantageous in several respects for the health, have however a fault: they prevent the iron from foods from being completely absorbed by the organism during digestion. A high daily consumption of tea may thus have consequences on iron assimilation by the organism.

However, tannin precipitation is not necessarily easy to carry out, and several chromatography steps are often necessary in order to recover and purify the tannins.

Another objective of the invention is thus to provide a natural product intended to be used in operations for clarifying a beverage such as tea, and more particularly intended to precipitate the tannins from tea.

The studies and research carried out by the inventors on the enological applications of yeasts and yeast derivatives have made it possible to develop a yeast extract rich in nucleic acids, and in particular in ribonucleic acids, having a size greater than 10 kDa, the use of which as a clarifier for winemaking products is more than promising.

Moreover, the research carried out by the inventors has also made it possible to discover, surprisingly, that this yeast extract rich in nucleic acids, and in particular in ribonucleic acids, is particularly suitable as a clarifier for teas, and in particular for precipitating the tannins from tea.

This discovery is all the more unexpected given that document WO 2016/010064 describes a yeast extract comprising at least 50% of RNA, for preventing the cloudiness of tea before said cloudiness appears, said cloudiness frequently occurring during the tea storage conditions.

Indeed, contrary to WO 2016/010064, the yeast extract rich in RNA is not used in the invention for preventing the appearance of cloudiness in tea, but for precipitating the visible and invisible particles from the tea, and in particular the tannins.

The inventors have also discovered, surprisingly, that this extract makes it possible to precipitate the pigments from tea.

A subject of the present invention is more particularly the use of a yeast extract comprising an amount by weight of nucleic acids of at least 10%, preferably of at least 15%, more preferentially of 20% to 95% and even more preferentially of 30% to 48% relative to the total weight of said extract, said nucleic acids being formed from fragments of ribonucleic acid (RNA) for clarifying musts and liquids, in particular beverages chosen from wine, tea, beer or fruit juices, and preferably wine or tea.

As previously described, the term "clarifying" is intended to mean the operation which consists in introducing, into the liquid to be clarified, a substance capable of flocculating and precipitating, said substance by flocculating and precipitating, dragging down all the suspended particles present in the liquid.

According to the invention, the clarifying is not intended to prevent or stop the cloudiness of the liquid, and in particular of the wine or of the tea, before it occurs, but on the contrary is intended to precipitate the visible or invisible particles present in said liquid.

Advantageously according to the invention, the use of a yeast extract rich in ribonucleic acids allows in particular the precipitation of the tannins from wine and from tea.

Just like the precipitation of the tannins from tea, the precipitation of the tannins from wine can prove to be advantageous in certain cases.

This is because the tannins of wine are responsible for the rough sensation in the mouth, and dry the mouth.

The term "yeast extract" is intended to mean the products resulting from the plasmolysis and lysis of intact yeast. The term "intact" yeast is intended to mean a live or deactivated "whole" yeast.

Yeast contains high amounts of ribonucleic acid (RNA). Generally, it is considered that ninety-nine percent by weight of the nucleic acids of a yeast are represented by the RNA. This RNA is 80% constituted of ribosomal RNA.

Ribonucleic acid (RNA) is a nucleic acid, that is to say a molecule consisting of a sequence of nucleotides.

Each nucleotide of the RNA consists:
of a pentose, the ribose, the carbon atoms of which are numbered from 1' to 5',
of a nucleic base or nitrogenous base (adenine "A", uracil "U", cytosine "C" and guanine "G"),
of a phosphate group.

The nitrogenous base (A, U, C or G) is connected by a nitrogen atom to carbon 1' of the ribose. The nucleotides are bonded to one another by phosphate groups, by means of phosphodiester bonds at the level of the 3' and 5' carbons.

According to the invention, a yeast extract as defined above, comprising in particular an amount by weight of ribonucleic acid of at least 10%, preferably of at least 15%, more preferentially of 20% to 95% and even more preferentially of 30% to 48%, relative to the total weight of said extract, will also, in the present application, be referred to as "yeast nucleic extract" ("YNE").

Each of said RNA fragments of the extract as defined above and as used according to the invention has an average molecular weight greater than 10 kDa, preferably ranging from 30 to 110 kDa.

Likewise according to the invention, the yeast nucleic extract as defined above and as used according to the invention also comprises mineral materials, saccharides (in particular glucans and mannans), and free amino acids.

By way of example, in a yeast nucleic extract:
the mineral materials are present in an amount by weight ranging from 5% to 30%, preferably from 15% to 25% relative to the total weight of the yeast extract;
the mannans are present in an amount by weight ranging from 5% to 25%, preferably from 10% to 20% relative to the total weight of the yeast extract;
the glucans are present in an amount by weight ranging from 1% to 10%, preferably from 3% to 8% relative to the total weight of the yeast extract;
the free amino acids are present in an amount by weight ranging from 1% to 10%, preferably from 3% to 8% relative to the total weight of the yeast extract.

According to the invention, the yeast extract as defined above and as used according to the invention may be in the form of a powder or of a more or less concentrated liquid, and preferably in the form of a powder.

According to the invention, the yeast is, for example, chosen from the group comprising *Saccharomyces, Kluyveromyces, Torula* and *Candida*, and is preferably *Saccharomyces*, and advantageously *Saccharomyces cerevisiae*.

The method for preparing the yeast extract as defined above and as used according to the invention advantageously makes it possible to preserve the RNA naturally present in the yeast.

The method for preparing a yeast extract (YNE) as defined above comprises the following steps:
mechanical, physical, osmotic, thermal, enzymatic plasmolysis and/or plasmolysis by pH modification of an intact yeast, in order, on the one hand, to free the internal macromolecules of said yeast in their native condition, and, on the other hand, to inactivate the enzymes for lysis of these macromolecules,
separation by centrifugation,
recovery of the soluble fraction containing the YNE,
optionally, drying of the soluble fraction.

The thermal plasmolysis will be carried out at a temperature sufficient to stop, inhibit the action of the enzymes for lysis of the internal macromolecules present in the yeast, and in particular of the nucleases, thereby advantageously making it possible to prevent the lysis of the nucleic chains, and thus to limit the formation of molecules of small molecular sizes.

The thermal plasmolysis step will, for example, be carried out at a temperature of from 60 to 120° C., preferably from 70° C. to 90° C., and even more preferentially at a temperature of 80° C., for a time ranging from 1 to 18 hours, preferably from 5 to 15 hours, and even more preferentially of 11 h.

The targeted enzymatic plasmolysis advantageously makes it possible to release the internal yeast macromolecules without cleaving them.

The plasmolysis by pH modification makes it possible to lyze the yeast and release its cell content.

Without wishing to be bound by any theory, the inventors are of the opinion that the plasmolysis makes it possible to damage the plasma membrane and the wall of the yeast cells to the extent of allowing openings that are sufficiently large to allow the nucleo protein complexes, namely the ribosomes, to come out.

According to one advantageous embodiment, a subject of the invention is the use of a yeast extract as defined above, for clarifying wines.

Advantageously, according to the invention, when the yeast nucleic extract is used for clarifying musts and wines, it will for example be used in the form of a powder. Said powder will for example be used at a content ranging from 0.1 g (gram) to 50 g per hectoliter (hl) of wine, and preferably from 5 to 30 g/hl.

The use of appropriate doses of the yeast nucleic extract of the invention allows rapid clarification and colloidal stability of the wine.

The use of excessive doses of the yeast nucleic extract of the invention risks resulting in an "over-clarifying" phenomenon, that is to say the presence, after clarifying, of the non-flocculated clarifier. Over-clarifying can, under poor storage conditions, generate cloudiness.

According to another advantageous embodiment, a subject of the invention is the use of a yeast extract as defined above, for clarifying tea, and in particular for precipitating the tannins from tea and/or the pigments from tea.

Advantageously, according to the invention, when the yeast nucleic extract is used for clarifying teas, it will for example be used in the form of a powder. Said powder will for example be used at a content ranging from 0.01 g (gram) to 5 g per liter (l) of tea, and preferably from 0.05 to 1 g/l.

The use of a yeast extract for precipitating the pigments from tea thus makes it possible to decolor the tea, which is sought in certain types of tea.

According to the invention, the nucleic yeast extracts as defined above have a minimum shelf life of 3 years in unopened packaging, stored in temperate premises that are not humid.

A subject of the invention is also the use of RNA fragments originating from a yeast chosen from the group comprising *Saccharomyces, Kluyveromyces, Torula* and *Candida* and mixtures thereof, for clarifying musts and liquids, in particular beverages chosen from wine, tea, beer or fruit juices.

According to one advantageous embodiment of the invention, the RNA fragments defined above are more particularly used for precipitating the tannins and/or pigments present in tea.

The present invention will now be illustrated by means of the examples and figures which follow, which are given by way of illustration and are thus in no way limiting.

The photos of FIGS. 1 and 2 illustrate the results, after 20 hours in a cold room, of the clarifying tests obtained with various clarifiers (respectively from left to right: "Control", "YPE", "YNE30" and "YNE95") on the wine "A" (FIG. 1) and the wine "B" (FIG. 2).

The photos of FIGS. 3, 4 and 5 illustrate the results, after 20 hours in a cold room, of the clarifying tests obtained with various clarifiers (respectively from left to right: "Control", "YPE", "YPE/YNE30" and "YNE30") on the "CRUDE" wine (FIG. 3), the wine "A" (FIG. 4) and the wine "B" (FIG. 5).

The photo of FIG. 6 illustrates the results of the clarifying test on the ice tea, and more particularly the results of the precipitation of the tannins from the ice tea, obtained after 18 hours at ambient temperature with the YNE30 clarifier at a concentration of 0.1 g/l.

The photos of FIG. 7 illustrate the results of the clarifying tests on the ice tea, and more particularly the results of precipitation of the tannins from the ice tea, obtained after 10 hours at a temperature of 6° C. (see respectively from left to right: "Control" (ice tea alone), "YPE" at a concentration of 1 g/l, "YNE30" at a concentration of 0.3 g/l and "YNE30" at a concentration of 1 g/l).

EXAMPLES 1 AND 2

Wine Clarifying Tests

The wines tested in examples 1 and 2 below are:
a "crude" wine (the most cloudy);
a wine "A";
a wine "B".

The products (clarifiers) tested are in powder form and are:
a "yeast protein extract", represented by "YPE", which serves as control (this YPE comprises in total approximately 13% of nucleotides and is described in "Revue des œnologues" ["Enologists' Review"], No. 120; pages 47-50, 2006);
a yeast nucleic extract of the invention comprising 30% by weight of ribonucleic acid, represented by "YNE30";
a yeast nucleic extract of the invention comprising 95% by weight of ribonucleic acid, represented by "YNE95";
a sample consisting of 50% of YPE and of 50% of YNE30, represented by "YPE/YNE30").

Example 1

Tube Tests

1) A first series of clarifying tests in wine is carried out with the following clarifiers: "YPE", "YNE30" and "YNE95" and on the following wines "A" (FIG. 1) and "B" (FIG. 2).

The clarifiers (in powder form) are incorporated at the maximum usable dose recommended for red wines or musts, namely 30 g of clarifier per hectoliter (hl) of wine/must.

The powders are pre-suspended diluted in 10 times their weight of water before incorporation into the wine. Thus, one gram (1 g) of clarifier is diluted in ten milliliters (10 ml) of distilled water.

An amount of thirty microliters (30 μl) of each clarifier thus diluted is incorporated into a test tube (except the control tube) comprising 10 ml of wine/must tested.

The objective is to demonstrate the differences in clarifying efficiency of the various clarifiers used at the same concentration and on two different samples of wine.

Figure 1:
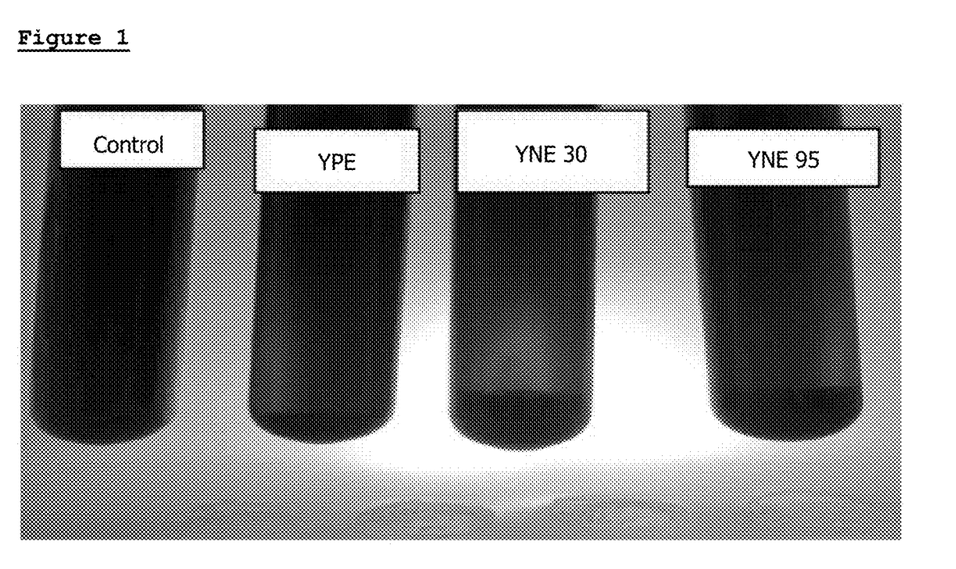
Figure 2:
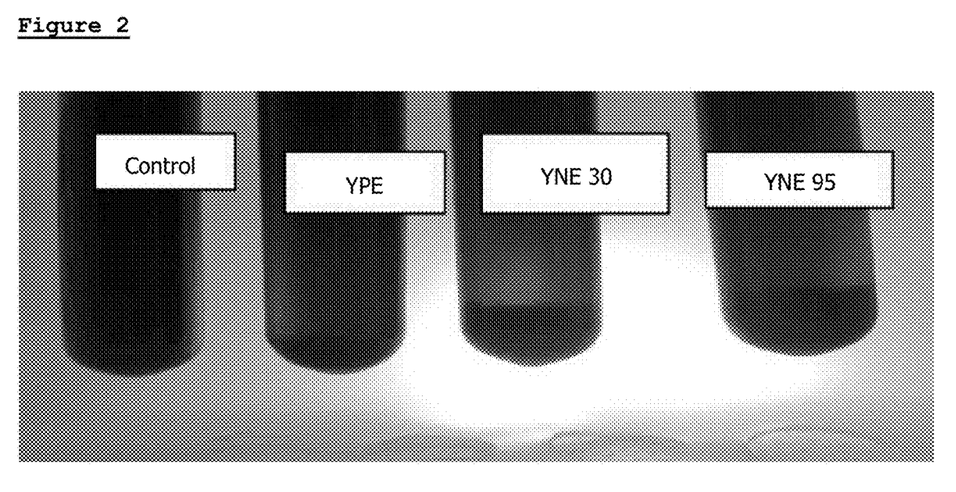

The results obtained after a 20-hour residence time of the tubes in a cold room (approximately+4° C.) are illustrated in FIGS. 1 (for the wine A) and 2 (for the wine B).

The bigger the decanting pellet observed in the test tube (i.e. the greater the decanting), the more satisfactory the clarifying.

The photos of FIGS. 1 and 2 show that, in the two cases, the control does not give a pellet since there is no natural decanting.

On the other hand, in the tubes comprising the clarifiers of the invention (YNE30 and YNE95), a decanting pellet is observed that is much larger (regardless of the wine tested) than in the tube comprising the prior art clarifier (YPE), which makes it possible to demonstrate better clarifying of the wine with the clarifiers of the invention compared with the prior art clarifier.

2) A second series of clarifying tests in wine is carried out with the following clarifiers: "YPE", "YPE/YNE30" and "YNE30", on the "crude" wine (FIG. 3), the wine "A" (FIG. 4) and the wine "B" (FIG. 5).

The clarifiers are prepared at the same concentration (30 g/hl) as described in section 1) above.

Figure 3:
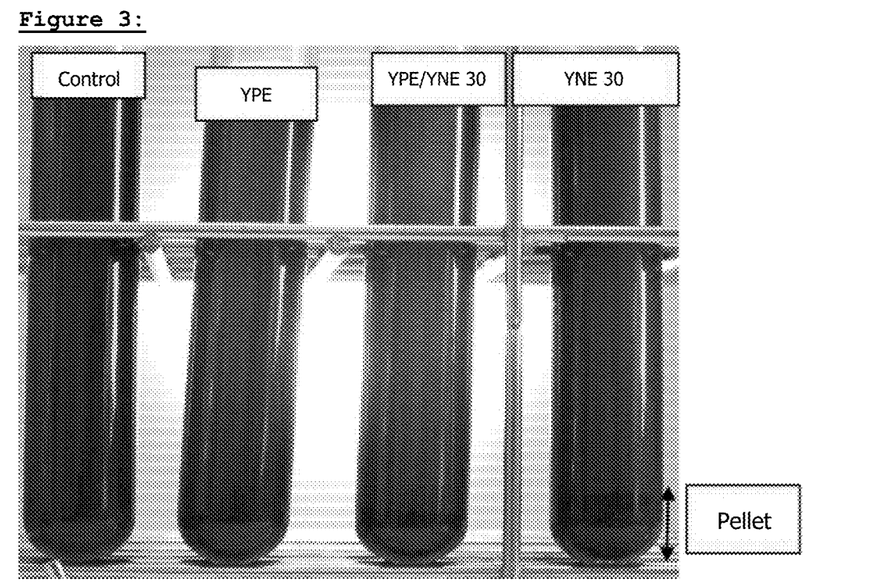
Figure 4:
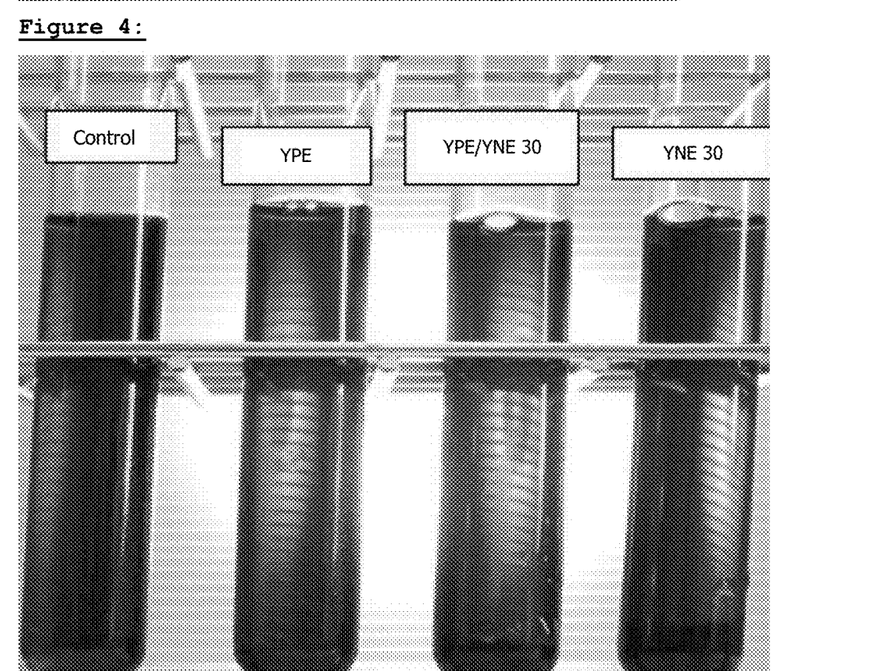

The results obtained after a 20-hour residence time of the tubes in a cold room (approximately +4° C.) are illustrated in FIGS. 3 (crude wine), 4 (wine A) and 5 (wine B).

Figure 5:
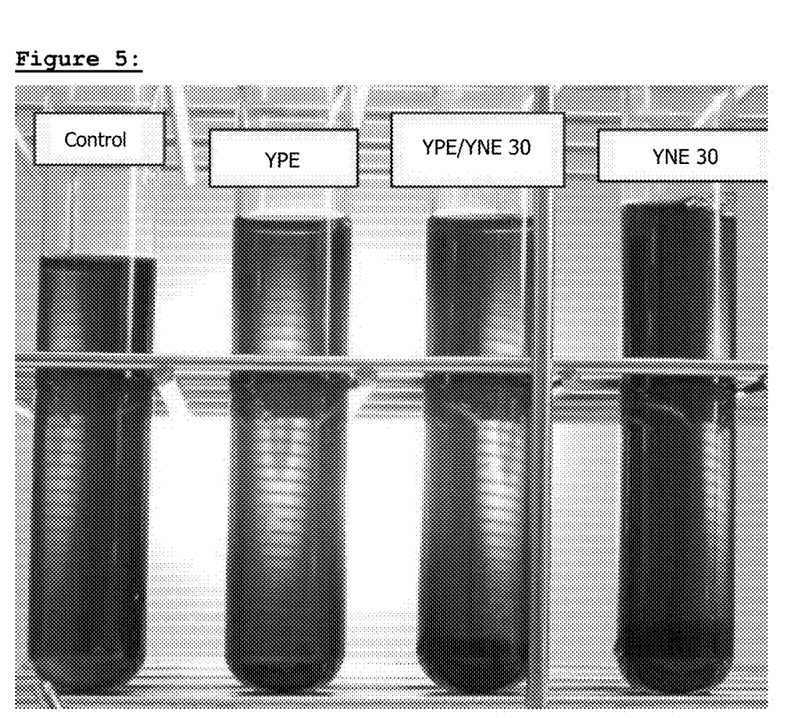

The photos of FIGS. 3 to 5 show that, in the three cases, the control does not show a pellet (no natural decanting).

The largest decanting pellet is observed with the "YNE30" clarifier of the invention, regardless of the wine tested (FIGS. 3 to 5).

A larger decanting pellet is also observed with the "YPE/YNE30" clarifier mixture than with the "YPE" prior art clarifier, regardless of the wine tested (FIGS. 3 to 5).

Thus, when a clarifier comprising a mixture of a clarifier of the invention and a clarifier of the prior art is prepared, this mixture makes it possible to improve the clarifying obtained with the clarifier of the prior art alone, not mixed with the clarifier of the invention.

3) Conclusion

The tests above demonstrate that the nucleic yeast extracts of the invention are clarifiers which are much more efficient for wines than the YPE natural clarifier of the prior art.

Moreover, the yeast nucleic extract of the invention has the important advantage of being simpler to produce than the YPE and of not requiring complex facilities.

Example 2

Spectro Cuvette Tests

Turbidity tests were carried out directly in a spectro cuvette.

As a reminder, turbidity, expressed in "NTU" (Nephelometric Turbidity Units), denotes the content of a fluid in terms of matter which makes it cloudy.

The "YNE30" and "YNE95" clarifiers of the invention are prepared at three different concentrations: 10 g/hl, 20 g/hl and 30 g/hl, by means of a prior dilution of each clarifier in distilled water (see previous example), followed by addition to the wine "B".

The initial turbidity of the wine "B" is 127 NTU.

The turbidity of said wine to which the clarifiers of the invention at various concentrations were added is measured after 48 hours in a cold room (+4° C.)

The results are given in table 1 below.

TABLE 1

|  | Wine B | Clarifier 10 g/hl | Clarifier 20 g/hl | Clarifier 30 g/hl |
|---|---|---|---|---|
| YNE95 | 127 NTU | 9.9 NTU | 10.2 NTU | 8.8 NTU |
| YNE30 | 127 NTU | 10.2 NTU | 11 NTU | 10.7 NTU |

The decrease in the turbidity is significant, for each of the two clarifiers, and regardless of their concentrations. The "YNE95" and "YNE30" clarifiers of the invention are each already very active at a concentration of 10 g/hl (decrease in the turbidity by a factor of 12).

A virtually identical clarification of the supernatants is noted after 48 hours, regardless of the concentration of the clarifiers of the invention.

The yeast extracts of the invention, rich in RNA, are thus very efficient as clarifiers in the wine sector.

EXAMPLE 3

Tea Clarifying Tests

The tea tested in this example is ice tea.

The objective of this example is to demonstrate, on the one hand, the precipitation of the tannins from the tea (which are found in the decanting pellet) and, on the other hand, the change in color of the tea.

The clarifier tested is in powder form and is YNE30.

Three samples having different concentrations are prepared, namely 0.1 g of YNE30 per liter of tea and 0.3 g of YNE30 per liter of tea and 1 g of YNE30 per liter of tea.

The powder is diluted beforehand in 10 times its weight of water. Thus, one gram of powder is diluted in 10 ml of distilled water.

The powder is totally soluble in the water; it is thus a clear solution that is added to the tea.

1) Test at Ambient Temperature

Figure 6:
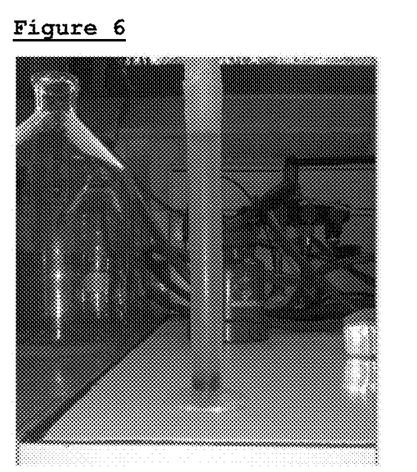

The YNE30 is introduced into a tube comprising ice tea (concentration prepared=0.1 g/l). The results obtained after 18 hours at ambient temperature are shown in FIG. 6.

The formation of a decanting pellet and a slight decoloration of the tea are observed.

The decanting pellet is removed using a pipette and is tasted by 3 individuals, including a flavorist.

The sensation noticed by each of the testers is astringency.

Since the sensation of astringency is provided by the tannins, it can be concluded from this that there has been good precipitation of the latter in the decanting pellet.

2) Test at 6° C.

The following four samples were tested:
ice tea alone (control),
ice tea into which has been introduced YPE at a concentration of 1 g/l,
ice tea into which has been introduced YNE 30 at a concentration of 0.3 g/l.
ice tea into which has been introduced YNE 30 at a concentration of 1 g/l.

Figure 7:
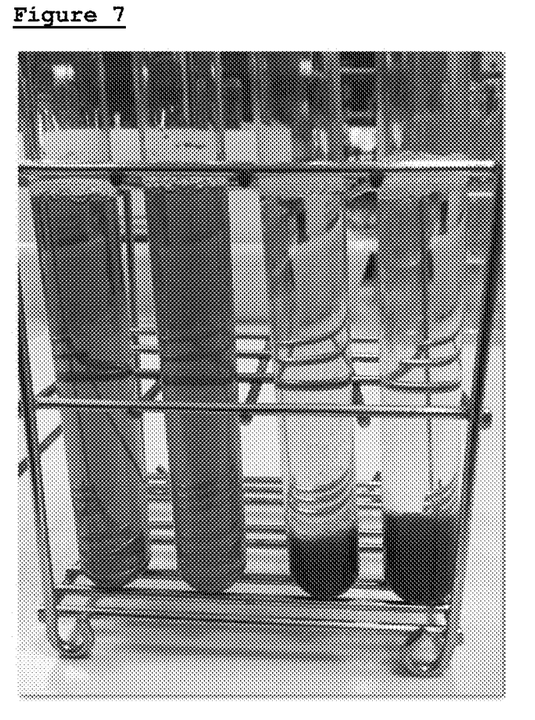

The results obtained after 10 hours at 6° C. are shown in FIG. 7.

The 4 samples described above are respectively represented from left to right in FIG. 7 (thus, the sample on the far left is the control, the one next to it is the one into which YPE has been introduced, etc.).

For the ice tea alone, no decanting or decoloration is observed.

For the ice tea into which has been introduced YPE (1 g/l), decanting and slight decoloration are observed after 2 to 3 months (as a reminder, FIG. 7 shows the results after 10 hours, therefore no decanting or decoloring observed), whereas, with the ice tea into which has been introduced YNE (at 0.3 and 1 g/l), a clear decanting and decoloring are observed after 3 to 6 hours.

The decanting pellet was removed by using a pipette and was tasted by the 3 testers mentioned in point 1 above.

The sensation noticed by each tester in terms of astringency is evaluated in table 2 below.

TABLE 2

|  | Ice tea as is | Ice tea + 1 g/l YPE | Ice tea + 0.3 g/l YNE | Ice tea + 1 g/l YNE |
|---|---|---|---|---|
| Decanting and decoloring | None | 2-3 months | 3-6 hours | 3-6 hours |
| Temperature | 6° C. | 6° C. | 6° C. | 6° C. |
| Tasting of the precipitation pellet: Sensation of astringency | 0 | 3 | 3 | 5 |

The sensation of astringency is slightly higher for the decanting pellet in the tube to which was added the YNE30 at a concentration of 0.3 g/l, compared with that felt by the tester for the decanting pellet in the tube to which was added the YNE30 at a concentration of 1 g/l.

Conclusion

After 10 hours, no difference was observed between the control sample (ice tea alone) and that to which was added the YPE at a concentration of 1 g/l. The addition of YPE to the ice tea does not make it possible to produce the precipitation of the tannins from the tea and/or the precipitation of the pigments from the tea.

On the other hand, the addition of YNE30 at concentrations such as 0.3 g/l or 1 g/l is sufficient to induce the precipitation of the tannins from the tea and of the pigments from the tea, this starting from 3 to 6 hours after the addition of YNE. The decoloring of the ice tea is clear for the tubes to which was added YNE30, regardless of the YNE concentration.

The addition of YNE30 at a concentration of 1 g/l to the ice tea results in a decanting pellet that is larger than with the addition of YNE30 at a concentration of 0.3 g/l.

Moreover, the sensation in terms of astringency is higher for the decanting pellet in the tube to which was added YNE at 1 g/l.

Since the sensation of astringency is provided by the tannins, it can be concluded from this that there has been good precipitation of the latter in the decanting pellet.

The invention claimed is:

1. A wine clarification method for clarifying cloudy wine having an unstable-particle load and comprising particles, wherein the particles are due to protein degradation or to microbiological growth, said method comprising flocculating and precipitating the particles in the wine, comprising contacting the wine comprising the particles with a yeast nucleic acids extract,
    wherein the yeast nucleic acids extract comprises ribonucleic acid (RNA) molecules in an amount by weight of 30% to 48% relative to the total weight of said yeast nucleic acids extract,
    wherein said RNA molecules of the yeast nucleic acids extract have an average molecular weight of greater than 10 kDa, and
    wherein said contacting results in flocculating and precipitating the particles and whereby the wine is clarified.

2. The method as claimed in claim 1, wherein the yeast nucleic acids extract additionally comprises mineral materials, saccharides, and free amino acids.

3. The method as claimed in claim 1, wherein the yeast nucleic acids extract is in a form comprising a powder or a concentrated liquid.

4. The method as claimed in claim 1, wherein yeast of the yeast nucleic acids extract comprises *Saccharomyces, Kluyveromyces, Torula* or *Candida*.

5. The method as claimed in claim 1, wherein the yeast nucleic acids extract is in the a form of comprising a powder and the contacting comprises adding from 0.1 g (gram) to 50 g of the yeast nucleic acids extract per hectoliter (hl) of wine.

6. The method as claimed in claim 1, wherein each of the molecules of RNA of the yeast nucleic acids extract has an average molecular weight from 30 to 110 kDa.

7. The method as claimed in claim 4, wherein each of the molecules of RNA of the yeast nucleic acids extract has an average molecular weight from 30 to 110 kDa.

8. The method as claimed in claim 1, wherein the yeast nucleic acids extract is a product of a plasmolysis.

9. The method as claimed in claim 1, wherein each of the molecules of RNA of the yeast nucleic acids extract has an average molecular weight from 30 to 110 kDa.

10. The method as claimed in claim 2, wherein each of the molecules of RNA of the yeast nucleic acids extract has an average molecular weight from 30 to 110 kDa.

11. The method as claimed in claim 3, wherein each of the molecules of RNA of the yeast nucleic acids extract has an average molecular weight from 30 to 110 kDa.

12. The method as claimed in claim 5, wherein each of the molecules of RNA of the yeast nucleic acids extract has an average molecular weight from 30 to 110 kDa.

13. The method as claimed in claim 8, wherein each of the molecules of RNA of the yeast nucleic acids extract has an average molecular weight from 30 to 110 kDa.

* * * * *